United States Patent
Suprise et al.

(10) Patent No.: US 6,572,601 B2
(45) Date of Patent: Jun. 3, 2003

(54) DISPOSABLE ABSORBENT ARTICLES HAVING AN ADJUSTABLE, PRETENSIONED WAISTBAND FASTENING SYSTEM

(75) Inventors: Jody Dorothy Suprise, Pine River, WI (US); Gary Lee Travis, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/326,300

(22) Filed: Jun. 4, 1999

(65) Prior Publication Data

US 2002/0058923 A1 May 16, 2002

(51) Int. Cl.⁷ ................................................. A61F 13/15
(52) U.S. Cl. ........................................ 604/391; 604/392
(58) Field of Search ............................... 604/385.3, 390, 604/385.01, 385.21, 385.23, 385.24, 385.02, 391, 392

(56) References Cited

U.S. PATENT DOCUMENTS

| | | |
|---|---|---|
| 1,079,479 A | 11/1913 | Earnshaw |
| 1,485,001 A | 2/1924 | Wills |
| 1,657,909 A | 1/1928 | Abramovich |
| 1,705,194 A | 3/1929 | Marinsky |
| 1,762,468 A | 6/1930 | Brewer |
| 1,963,334 A | 6/1934 | Neilson |
| 2,201,255 A | 5/1940 | Wilson, Jr. |
| 2,242,977 A | 5/1941 | Marcos |
| 2,475,175 A | 7/1949 | Cadous |
| 2,477,914 A | 8/1949 | Webb |
| 2,545,761 A | 3/1951 | Brink |
| 2,570,963 A | 10/1951 | Mesmer |
| 2,630,120 A | 3/1953 | Nielson |
| 2,630,806 A | 3/1953 | Kiscaden |
| 2,743,725 A | 5/1956 | Matthews |

(List continued on next page.)

FOREIGN PATENT DOCUMENTS

| | | |
|---|---|---|
| AU | 667899 | 4/1996 |
| CA | 2187021 A1 | 10/1995 |
| CA | 2187366 A1 | 10/1995 |
| CA | 2096672 C | 11/1997 |
| CA | 2103992 C | 7/1998 |
| EP | 0 206 208 B1 | 12/1986 |
| EP | 0 217 032 A2 | 4/1987 |
| EP | 0 251 251 A3 | 1/1988 |
| EP | 0 463 276 A1 | 1/1992 |
| EP | 0 532 034 A2 | 3/1993 |

(List continued on next page.)

OTHER PUBLICATIONS

Derwent World Patent Database abstract of FR 2762507 A1: Description of RAHALA, "Baby's Disposable Nappy.".

(List continued on next page.)

Primary Examiner—Dennis Ruhl
Assistant Examiner—Jamisue A Webb
(74) Attorney, Agent, or Firm—Jeffrey B Curtin; Alyssa A Dudkowski

(57) ABSTRACT

A prefastened disposable absorbent article includes a pair of primary fasteners which are located on the opposed side edges in one the waist regions of the article. The primary fasteners overlap and releasably engage the opposite waist region of the absorbent article to provide the prefastened absorbent article. The prefastened disposable absorbent article further includes at least one secondary fastener and a belt which are configured to provide a pretensioned waistband and are capable of elongating to releasably engage the opposite waist region of the absorbent article to further conform the waist regions of the article to a wearer's body after the article has been pulled on over the hips of the wearer.

43 Claims, 7 Drawing Sheets

U.S. PATENT DOCUMENTS

| | | |
|---|---|---|
| 2,801,632 A | 8/1957 | Burner et al. |
| 2,808,831 A | 10/1957 | Winslett |
| 2,830,589 A | 4/1958 | Doner |
| 2,833,282 A | 5/1958 | Moore |
| 2,910,982 A | 11/1959 | Woodward |
| 2,931,361 A | 4/1960 | Sostrin |
| 3,039,466 A | 6/1962 | Wilson |
| 3,077,193 A | 2/1963 | Mann |
| 3,610,244 A | 10/1971 | Jones, Sr. |
| 3,638,651 A | 2/1972 | Torr |
| 3,653,381 A | 4/1972 | Warnken |
| 3,825,006 A | 7/1974 | Ralph |
| 3,882,871 A | 5/1975 | Taniguchi |
| 4,024,867 A | 5/1977 | Mesek |
| 4,051,853 A | 10/1977 | Egan, Jr. |
| 4,051,854 A | 10/1977 | Aaron |
| 4,066,081 A | 1/1978 | Schaar |
| 4,074,716 A | 2/1978 | Schaar |
| 4,089,068 A | 5/1978 | Swallow |
| 4,090,516 A | 5/1978 | Schaar |
| 4,205,679 A | 6/1980 | Repke et al. |
| 4,210,143 A | 7/1980 | De Jonckheere |
| 4,315,508 A | 2/1982 | Bolick |
| 4,337,771 A | 7/1982 | Pieniak et al. |
| 4,409,049 A | 10/1983 | Passafiume et al. |
| 4,410,327 A | 10/1983 | Baggaley |
| 4,500,316 A | 2/1985 | Damico |
| 4,515,595 A | 5/1985 | Kievit et al. |
| 4,522,853 A | 6/1985 | Szonn et al. |
| 4,525,407 A | 6/1985 | Ness |
| 4,563,185 A | 1/1986 | Reiter |
| 4,568,341 A | 2/1986 | Mitchell et al. |
| 4,581,772 A | 4/1986 | Smith |
| 4,596,055 A | 6/1986 | Aach et al. |
| 4,598,528 A | 7/1986 | McFarland et al. |
| 4,604,096 A | 8/1986 | Dean et al. |
| 4,610,680 A | 9/1986 | LaFleur |
| 4,610,681 A | 9/1986 | Strohbeen et al. |
| 4,615,695 A | 10/1986 | Cooper |
| 4,617,022 A | 10/1986 | Pigneul et al. |
| 4,619,649 A | 10/1986 | Roberts |
| 4,623,339 A | 11/1986 | Ciraldo et al. |
| 4,630,320 A | 12/1986 | Van Gompel |
| 4,663,220 A | 5/1987 | Wisneski et al. |
| 4,675,918 A | 6/1987 | O'Brien |
| D290,780 S | 7/1987 | Wistrand |
| 4,699,622 A | 10/1987 | Toussant et al. |
| 4,704,116 A | 11/1987 | Enloe |
| 4,726,874 A | 2/1988 | Van Vliet |
| 4,728,326 A | 3/1988 | Gilles |
| 4,743,239 A | 5/1988 | Cole |
| 4,747,846 A | 5/1988 | Boland et al. |
| 4,753,646 A | 6/1988 | Enloe |
| 4,753,650 A | 6/1988 | Williams |
| 4,798,603 A | 1/1989 | Meyer et al. |
| 4,801,485 A | 1/1989 | Sallee et al. |
| 4,808,252 A | 2/1989 | Lash |
| 4,826,499 A | 5/1989 | Ahr |
| 4,850,988 A | 7/1989 | Aledo et al. |
| 4,850,992 A | 7/1989 | Amaral et al. |
| 4,857,067 A | 8/1989 | Wood et al. |
| 4,883,481 A | 11/1989 | Blanchard |
| 4,892,598 A | 1/1990 | Stevens et al. |
| 4,895,569 A | 1/1990 | Wilson et al. |
| 4,904,252 A | 2/1990 | Fitzgerald |
| 4,908,247 A | 3/1990 | Baird et al. |
| 4,909,802 A | 3/1990 | Ahr et al. |
| 4,911,702 A | 3/1990 | O'Leary et al. |
| 4,917,682 A | 4/1990 | Lancaster et al. |
| 4,936,840 A | 6/1990 | Proxmire |
| 4,937,887 A | 7/1990 | Schreiner |
| 4,938,753 A | 7/1990 | Van Gompel et al. |
| 4,944,733 A | 7/1990 | Casale |
| 4,961,736 A | 10/1990 | McCloud |
| 4,964,860 A | 10/1990 | Gipson et al. |
| 4,973,326 A | 11/1990 | Wood et al. |
| 4,988,346 A | 1/1991 | Pfefferkorn |
| 4,998,929 A | 3/1991 | Bjorksund et al. |
| 5,019,072 A | 5/1991 | Polski |
| 5,019,073 A | 5/1991 | Roessler et al. |
| 5,040,244 A | 8/1991 | Tubbs |
| 5,062,839 A | 11/1991 | Anderson |
| 5,066,289 A | 11/1991 | Polski |
| 5,069,678 A | 12/1991 | Yamamoto et al. |
| 5,074,854 A | 12/1991 | Davis |
| 5,087,253 A | 2/1992 | Cooper |
| 5,106,382 A | 4/1992 | Henry |
| 5,106,385 A | 4/1992 | Allen et al. |
| 5,110,403 A | 5/1992 | Ehlert |
| 5,112,326 A | 5/1992 | Quadrini |
| 5,135,522 A | 8/1992 | Fahrenkrug et al. |
| 5,140,757 A | 8/1992 | Terada |
| 5,163,932 A | 11/1992 | Nomura et al. |
| 5,170,505 A | 12/1992 | Rohrer |
| 5,176,668 A | 1/1993 | Bernardin |
| 5,176,670 A | 1/1993 | Roessler et al. |
| 5,176,672 A | 1/1993 | Bruemmer et al. |
| 5,185,011 A | 2/1993 | Strasser |
| 5,186,779 A | 2/1993 | Tubbs |
| 5,187,817 A | 2/1993 | Zolner |
| 5,192,606 A | 3/1993 | Proxmire et al. |
| 5,226,992 A | 7/1993 | Morman |
| 5,236,430 A | 8/1993 | Bridges |
| 5,242,436 A | 9/1993 | Weil et al. |
| 5,246,433 A | 9/1993 | Hasse et al. |
| 5,275,590 A | 1/1994 | Huffman et al. |
| 5,300,057 A | 4/1994 | Miller et al. |
| 5,304,162 A | 4/1994 | Kuen |
| 5,312,387 A | 5/1994 | Rossini et al. |
| 5,340,431 A | 8/1994 | Terada |
| 5,358,500 A | 10/1994 | Lavon et al. |
| 5,368,584 A | 11/1994 | Clear et al. |
| 5,368,585 A | 11/1994 | Dokken |
| 5,370,632 A | 12/1994 | Beplate |
| 5,370,634 A | 12/1994 | Ando et al. |
| 5,373,587 A | 12/1994 | Sexton |
| 5,374,262 A | 12/1994 | Keuhn, Jr. et al. |
| 5,383,872 A | 1/1995 | Roessler et al. |
| 5,386,595 A | 2/1995 | Kuen et al. |
| 5,397,639 A | 3/1995 | Tollini |
| 5,399,219 A | 3/1995 | Roessler et al. |
| 5,401,275 A | 3/1995 | Flug et al. |
| 5,409,476 A | 4/1995 | Coates |
| 5,423,789 A | 6/1995 | Kuen |
| 5,445,628 A | 8/1995 | Gipson et al. |
| 5,451,219 A | 9/1995 | Suzuki et al. |
| 5,462,541 A | 10/1995 | Bruemmer et al. |
| 5,489,282 A | 2/1996 | Zehner et al. |
| 5,496,298 A | 3/1996 | Kuepper et al. |
| 5,499,978 A | 3/1996 | Buell et al. |
| 5,500,063 A | 3/1996 | Jessup |
| 5,509,915 A | 4/1996 | Hanson et al. |
| 5,527,302 A | 6/1996 | Endres et al. |
| H1558 H | 7/1996 | Goulait et al. |
| 5,531,731 A | 7/1996 | Brusky |
| 5,531,732 A | 7/1996 | Wood |
| 5,537,722 A | 7/1996 | Niederhofer et al. |
| 5,540,796 A | 7/1996 | Fries |
| 5,545,158 A | 8/1996 | Jessup |
| 5,545,275 A | 8/1996 | Herrin et al. |
| 5,549,592 A | 8/1996 | Fries et al. |

| | | | |
|---|---|---|---|
| 5,554,146 A | 9/1996 | Niederhofer et al. | |
| 5,562,650 A | 10/1996 | Everett et al. | |
| 5,569,232 A | 10/1996 | Roe et al. | |
| 5,569,234 A | 10/1996 | Buell et al. | |
| 5,571,586 A | 11/1996 | Gobran | |
| 5,575,784 A | 11/1996 | Ames-Ooten et al. | |
| 5,582,606 A | 12/1996 | Bruemmer et al. | |
| 5,591,152 A | 1/1997 | Buell et al. | |
| 5,593,401 A | 1/1997 | Sosalla et al. | |
| 5,601,546 A | 2/1997 | Tanji et al. | |
| 5,605,735 A | 2/1997 | Zehner et al. | |
| 5,607,416 A | 3/1997 | Yamamoto et al. | |
| 5,611,789 A | 3/1997 | Seth | |
| 5,618,366 A | 4/1997 | Suekane | |
| 5,624,420 A | 4/1997 | Bridges et al. | |
| 5,624,424 A | 4/1997 | Saisaka et al. | |
| 5,624,428 A | 4/1997 | Sauer | |
| 5,624,429 A | 4/1997 | Long et al. | |
| 5,626,574 A | 5/1997 | Sasaki et al. | |
| 5,628,738 A | 5/1997 | Suekane | |
| 5,629,063 A | 5/1997 | Gobran | |
| 5,634,916 A | 6/1997 | Lavon et al. | |
| H1674 H | 8/1997 | Ames et al. | |
| 5,656,111 A | 8/1997 | Dilnik et al. | |
| 5,662,637 A | 9/1997 | Kitaoka et al. | |
| 5,662,638 A | 9/1997 | Johnson et al. | |
| 5,665,084 A | 9/1997 | Richmond | |
| 5,669,897 A | 9/1997 | Lavon et al. | |
| 5,685,873 A | 11/1997 | Bruemmer | |
| 5,685,874 A | 11/1997 | Buell et al. | |
| 5,690,626 A | 11/1997 | Suzuki et al. | |
| 5,690,627 A | 11/1997 | Clear et al. | |
| 5,693,038 A | 12/1997 | Suzuki et al. | |
| 5,695,488 A * | 12/1997 | Sosalla | 604/385.2 |
| 5,695,868 A | 12/1997 | McCormack | |
| D389,320 S | 1/1998 | Vinnage et al. | |
| 5,707,364 A | 1/1998 | Coates | |
| 5,711,832 A | 1/1998 | Glaug et al. | |
| 5,725,518 A | 3/1998 | Coates | |
| 5,759,317 A | 6/1998 | Justmann | |
| 5,772,649 A | 6/1998 | Siudzinski | |
| 5,772,825 A | 6/1998 | Schmitz | |
| 5,788,685 A | 8/1998 | Ronnberg et al. | |
| 5,788,797 A | 8/1998 | Herrin et al. | |
| 5,795,433 A | 8/1998 | Niedermeyer | |
| 5,827,259 A | 10/1998 | Laux et al. | |
| 5,827,260 A | 10/1998 | Suzuki et al. | |
| 5,830,206 A | 11/1998 | Larsson | |
| 5,843,056 A | 12/1998 | Good et al. | |
| 5,855,574 A | 1/1999 | Kling et al. | |
| 5,876,531 A | 3/1999 | Jacobs et al. | |
| 5,897,545 A | 4/1999 | Kline et al. | |
| 5,899,896 A | 5/1999 | Suprise et al. | |
| 5,904,802 A | 5/1999 | Niedermeyer | |
| 5,916,203 A | 6/1999 | Brandon et al. | |
| 5,916,207 A | 6/1999 | Toyoda et al. | |
| 5,919,334 A | 7/1999 | Niedermeyer | |
| 5,944,707 A * | 8/1999 | Ronn | 604/386 |
| 5,961,761 A * | 10/1999 | Heindel et al. | 156/163 |
| 5,971,153 A | 10/1999 | Bauer et al. | |
| 6,022,430 A | 2/2000 | Blenke et al. | |
| 6,022,431 A | 2/2000 | Blenke et al. | |
| 6,022,432 A | 2/2000 | Elsberg et al. | |
| 6,030,373 A | 2/2000 | VanGompel et al. | |
| 6,036,805 A | 3/2000 | McNichols | |
| 6,045,543 A | 4/2000 | Pozniak et al. | |
| 6,113,717 A | 9/2000 | Vogt et al. | |
| 6,149,638 A | 11/2000 | Vogt et al. | |
| 6,287,287 B1 | 9/2001 | Elsberg | |
| 6,322,552 B1 | 11/2001 | Blenke et al. | |

FOREIGN PATENT DOCUMENTS

| | | |
|---|---|---|
| EP | 0597331 A1 | 5/1994 |
| EP | 0 544 703 B1 | 9/1994 |
| EP | 0 696 911 B1 | 1/1997 |
| EP | 0 753 292 A2 | 1/1997 |
| EP | 0 487 758 B1 | 3/1997 |
| EP | 0 809 992 A1 | 12/1997 |
| EP | 0 878 180 A2 | 11/1998 |
| FR | 2566631 | 3/1984 |
| GB | 1 520 740 | 8/1978 |
| GB | 2 244 422 B | 12/1991 |
| GB | 2 267 024 B | 11/1993 |
| GB | 2 288 314 A | 10/1995 |
| GB | 2 288 315 A | 10/1995 |
| GB | 2 288 316 A | 10/1995 |
| GB | 2 291 783 A | 2/1996 |
| GB | 2 294 867 A | 5/1996 |
| GB | 2 297 473 A | 6/1996 |
| GB | 2 308 290 A | 6/1997 |
| GB | 2 308 290 B | 6/1999 |
| JP | 6-77718 U | 11/1994 |
| JP | 7-213553 A | 8/1995 |
| JP | 7-227407 A | 8/1995 |
| JP | 7-255773 A | 10/1995 |
| JP | 7-299094 A | 11/1995 |
| JP | 8-229072 A | 9/1996 |
| JP | 9-287 U | 5/1997 |
| JP | 11-47188 A | 2/1999 |
| WO | WO 83/04163 A1 | 12/1983 |
| WO | WO 90/07313 A1 | 7/1990 |
| WO | WO 91/04724 A1 | 4/1991 |
| WO | WO 91/08725 A1 | 6/1991 |
| WO | WO 92/22274 A1 | 12/1992 |
| WO | WO 93/09742 A1 | 5/1993 |
| WO | WO 94/17768 A1 | 8/1994 |
| WO | WO 95/01148 A1 | 1/1995 |
| WO | WO 95/02383 A1 | 1/1995 |
| WO | WO 95/13772 A1 | 5/1995 |
| WO | WO 95/22951 A1 | 8/1995 |
| WO | WO 95/27460 A1 | 10/1995 |
| WO | WO 95/27462 A1 | 10/1995 |
| WO | WO 95/29657 A1 | 11/1995 |
| WO | WO 96/03101 A1 | 2/1996 |
| WO | WO 96/18315 A1 | 6/1996 |
| WO | WO 96/29037 | 9/1996 |
| WO | WO 96/32084 A1 | 10/1996 |
| WO | WO 97/15260 A1 | 5/1997 |
| WO | WO 97/23186 A1 | 7/1997 |
| WO | WO 97/25951 A1 | 7/1997 |
| WO | WO 97/31605 A1 | 9/1997 |
| WO | WO 97/32555 A1 | 9/1997 |
| WO | WO 97/33547 A1 | 9/1997 |
| WO | WO 97/46197 A1 | 12/1997 |
| WO | WO 97/47265 A1 | 12/1997 |
| WO | WO 97/48357 | 12/1997 |
| WO | WO 98/03140 A1 | 1/1998 |
| WO | WO 98/18421 A1 | 5/1998 |
| WO | WO 98/29251 A1 | 7/1998 |
| WO | WO 98/51252 | 11/1998 |
| WO | WO 98/56328 A1 | 12/1998 |
| WO | WO 99/07319 A1 | 2/1999 |
| WO | WO 99/56688 | 11/1999 |
| WO | WO 99/65438 | 12/1999 |
| WO | WO 99/65442 | 12/1999 |
| WO | WO 00/37010 | 6/2000 |
| WO | WO 01/43682 A1 | 6/2001 |
| WO | WO 01/43683 A1 | 6/2001 |
| WO | WO 01/70155 A1 | 9/2001 |

OTHER PUBLICATIONS

Derwent World Patent Database abstract of JP 11–070143 A: Description of TOYO EISAI KK (TOEI–N), "Disposable Diaper For Adults and Childrend.".

Derwent World Patent Database abstract of JP 11–076299 A: Description of UNICHARM KK (UNIC–N), "Disosable Diaper.".

Derwent World Patent Database abstract of JP 6–063076 A: Description of Kao Corp. (Kaos), "Throw Away Diaper or Nappy.".

Derwent World Patent Database abstract of JP 9–276334 A: Descritpion of Kao Corp (Kaos), "Disposable Baby Nappy.".

Derwent World Patent Database abstract of JP 95–044941 B2: Description of ZUIKO KK (ZUIK–N), "Simple Solid Diaper For Eliminating Waste of Material by Using Square Shape.".

* cited by examiner

DISPOSABLE ABSORBENT ARTICLES HAVING AN ADJUSTABLE, PRETENSIONED WAISTBAND FASTENING SYSTEM

FIELD OF THE INVENTION

The present invention relates to disposable absorbent articles which are adapted to contain body exudates. More particularly, the present invention relates to prefastened disposable absorbent articles which have an adjustable, pretensioned waistband fastening system to maintain the articles about the waist of the wearer.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the care giver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Conventional diapers are not provided in a prefastened condition and have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the outer surface of the outer cover of the diaper in the front waist portion of the diaper. In such a configuration, the diaper has been positioned between the legs of the wearer and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the caregiver. However, such conventional diapers are not prefastened before use and thus are not configured to be pulled up or down over the hips of the wearer when the fasteners are attached.

Several attempts have been made to provide absorbent articles which effectively contain body exudates and are capable of being pulled up or down over the hips of the wearer. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such training pant articles have not contained bodily exudates as effectively as conventional diaper-type articles which can be adjusted to achieve a more conforming fit to the wearer. Moreover, the removal of soiled absorbent articles which have integral side panels, such as conventional training pants, has not always been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles which can provide the benefits of conventional training pants and conventional diapers. That is, there remains a need for absorbent articles which conform to the wearer to effectively contain bodily exudates, which are capable of being pulled up and down over the hips and buttocks of the wearer, and which are readily secured about and removed from the wearer in a convenient and clean manner. In particular, there is a need for disposable absorbent articles which include waist sections which may be releasably prefastened such that the article can be reliably pulled on over the wearers legs and hips and which are adjustable once in the proper position to provide a close, conforming fit about the waist of the wearer.

SUMMARY OF THE INVENTION

In response to the difficulties and problems discussed above, a new prefastened disposable absorbent article which has an adjustable, pretensioned waistband fastening system has been discovered. In one aspect, the present invention concerns a prefastened disposable absorbent article which includes a pair of primary fasteners which are located on opposed side edges of the article in one of the waist regions and which overlap and releasably engage the opposite waist region of the absorbent article to provide the prefastened absorbent article. The prefastened absorbent article also includes a belt located in one of the waist regions which is capable of being elongated and which provides a pretension on the waist region when the primary fasteners are releasably engaged. The belt includes opposed end portions, a latent segment and an elastic segment.

In a particular embodiment, the absorbent article includes at least one secondary fastener attached to one of the end portions of the belt. Upon elongation of the belt, the secondary fastener is configured to releasably engage the opposite waist region to conform the waist regions to the wearer's body after the prefastened absorbent article is pulled on over a wearer's hips. The absorbent article may also include a pair of secondary fasteners attached to the opposed end portions of the belt. In such a configuration, the secondary fasteners and opposed end portions of the belt are configured to extend over the primary fasteners to releasably engage the opposite waist region of the absorbent article to conform the waist regions to the wearer's body after the prefastened absorbent article is pulled on over a wearer's hips.

In another aspect, the present invention provides a prefastened disposable absorbent article which defines a front waist region, a back waist region, a crotch region which extends between and connects the waist regions and a pair of opposed side edges. The absorbent article includes an outer cover, an absorbent chassis which is connected to the outer cover, a pair of primary fasteners and a belt with a pair of secondary fasteners attached thereto. The absorbent chassis includes a bodyside liner and an absorbent core disposed between the outer cover and the bodyside liner. The primary fasteners are located on the laterally opposed side edges of the back waist region of the absorbent article and are configured to releasably engage an outer surface of the absorbent article in the front waist region of the absorbent article. The belt is located in the back waist region of the absorbent article and defines a pair of opposed end portions, a pair of opposed elastic segments and a latent segment between the elastic segments. The secondary fasteners are located on the opposed end portions of the belt and are configured to releasably engage the outer surface of the front waist region to further conform the waist regions to a wearer's body after the prefastened absorbent article is pulled on over a wearer's hips.

In still another aspect, the present invention provides a prefastened disposable absorbent article which defines an absorbent, a front waist region, a back waist region, a crotch region which extends between and connects the waist regions and a pair of opposed side edges. The absorbent article includes a pair of primary fasteners and a waist size adjustment mechanism. The primary fasteners are located on the opposed side edges in one of the waist regions and are releasably engaged to the opposite waist region of the disposable absorbent article thereby defining a waist perimeter dimension. The waist size adjustment mechanism is located in one of the waist regions and provides an initial pretension on the waist regions of the absorbent article when the absorbent article is at the waist perimeter dimension. In use, the waist size adjustment mechanism is also capable of reducing the waist perimeter dimension of the absorbent article without releasing the primary fasteners to conform the waist regions to a wearer's body after the prefastened absorbent article has been pulled on.

In another aspect, the present invention provides a package of prefastened disposable absorbent articles containing absorbent articles of the different aspects of the present invention.

In most embodiments, the belt generally defines a first length when applied to the absorbent article and a second length which is less than the first length after the latent segment is activated to provide the pretension on the waist region. The belt is also capable of being elongated to a third length which is greater than the first length. The latent segment of the belt may be provided by a latent material which may or may not be elastically extensible after activation. In a particular embodiment, the belt includes two elastic segments and the latent segment is located between the two elastic segments.

The present invention advantageously provides a prefastened disposable absorbent article which includes an adjustable, pretensioned waistband fastening system for improved fit and performance. The absorbent article of the present invention is capable of being reliably pulled up or down over the hips of the wearer to assist in the toilet training of the wearer similar to conventional training pants. The pretensioned waistband fastening system allows the waist of the article to expand while being pulled on over the hips of the wearer while still providing tension for a close fit at the waist after the article is in proper position on the wearer. Moreover, the adjustability of the waistband fastening system allows the caregiver to cinch up the waist of the article for a closer more conforming fit if desired. Further, similar to conventional diapers, the absorbent article of the present invention can advantageously be applied to and removed from the wearer after it has been soiled with relative ease and cleanliness.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns prefastened disposable absorbent articles which are configured to closely conform to the body of the wearer to effectively contain body exudates while being capable of being pulled up or down over the hips and buttocks of the wearer. The prefastened disposable absorbent articles can also be easily secured to and removed directly from the waist of the wearer. As such, the absorbent articles of the present invention can function similar to conventional training pants in their prefastened configuration or they can be unfastened prior to or during use to function similar to conventional diapers.

The prefastened disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse. The prefastened disposable absorbent articles of the present invention will be described in terms of a prefastened disposable diaper article which is adapted to be worn by young children or infants about the lower torso. It is understood that the disposable absorbent articles of the present invention are equally adaptable for use as other types of absorbent articles such as adult incontinent products, training pants, feminine hygiene products, other personal care or health care garments, and the like.

Figure 1:
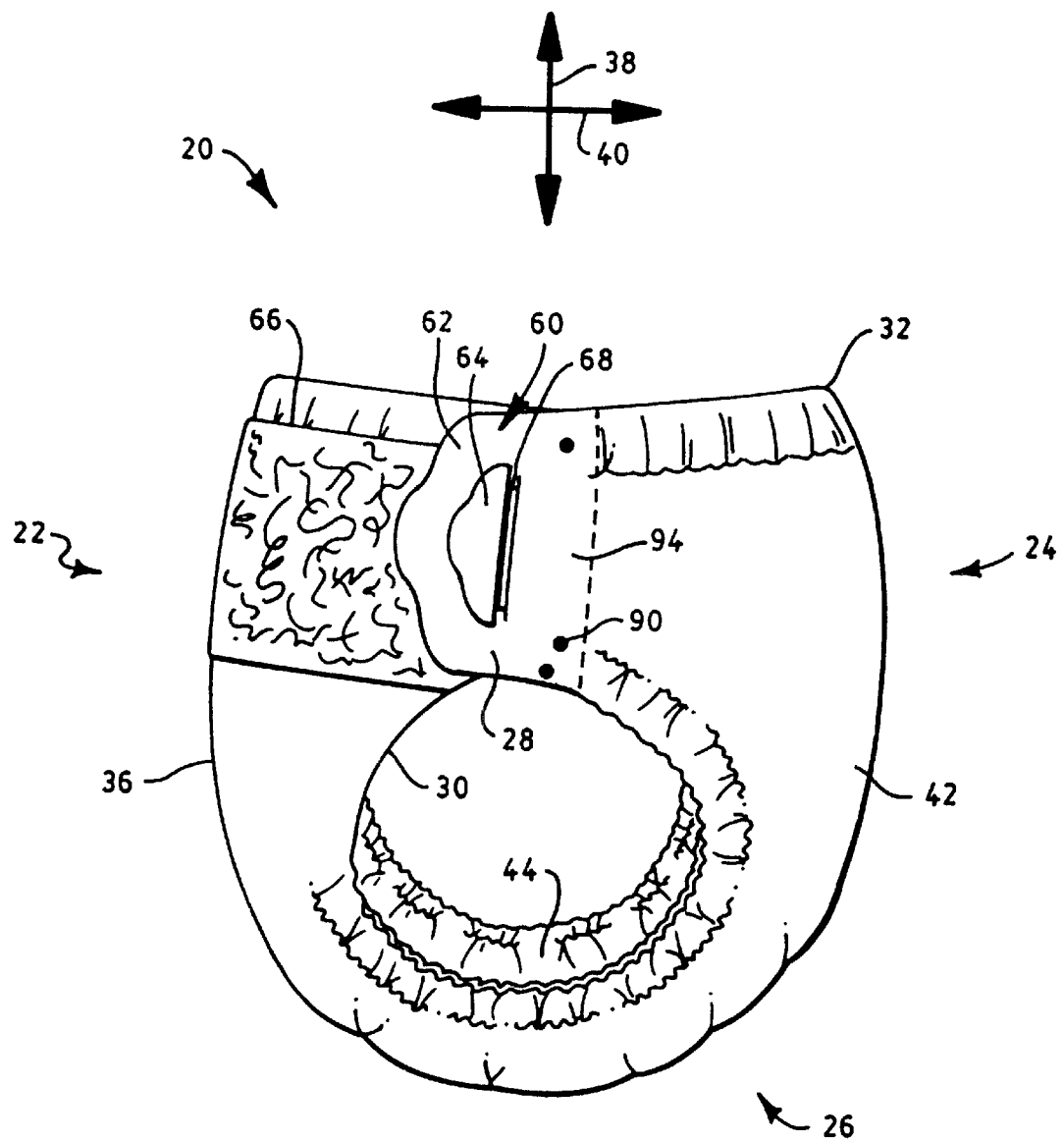
FIG. 1 representatively shows a side view of an example of a prefastened disposable absorbent article according to the present invention.
Figure 2:
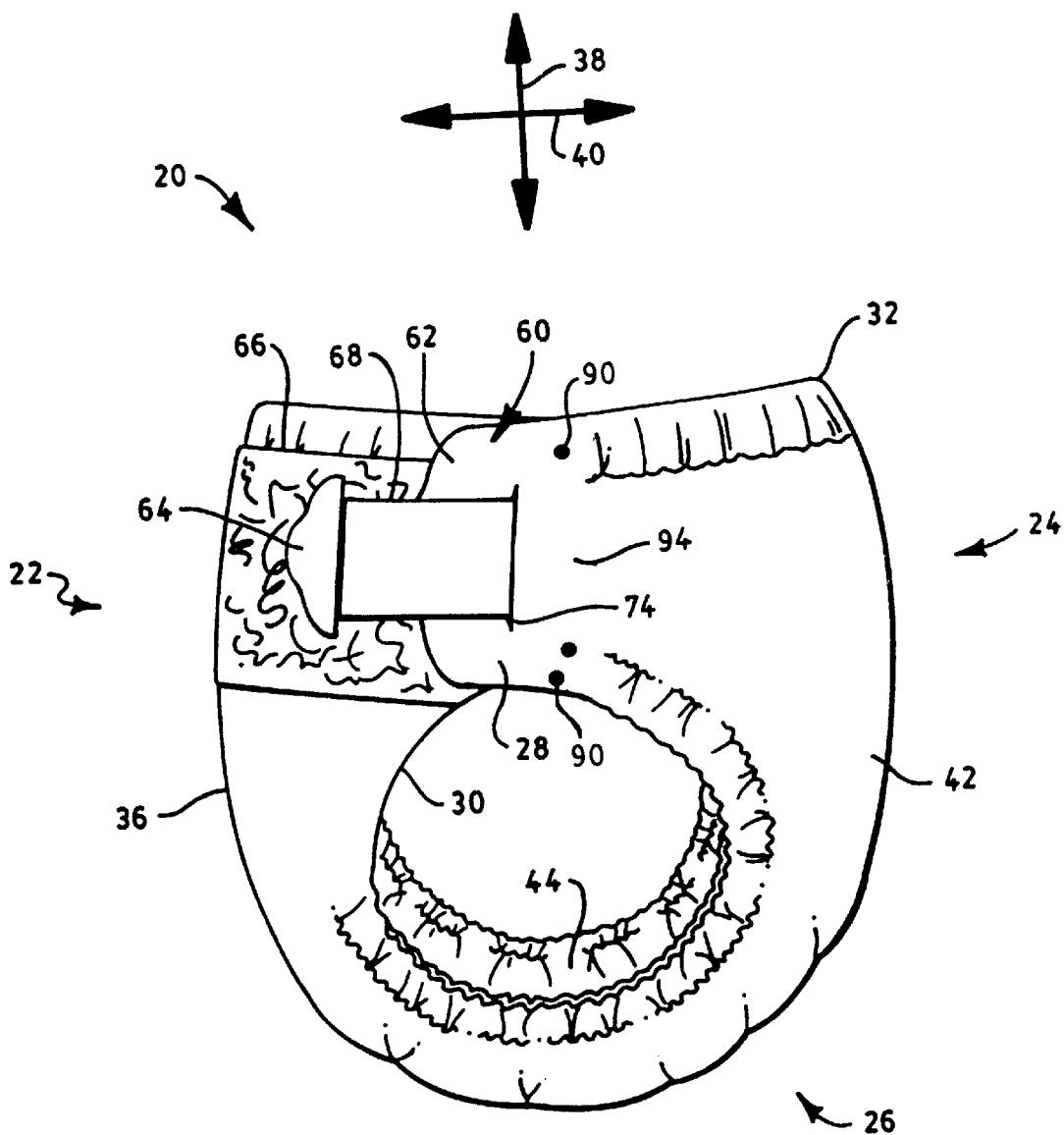
FIG. 2 representatively shows a side view of the disposable absorbent article of FIG. 1 wherein the secondary fasteners have been extended and engaged to conform the waist regions of the article to the waist of the wearer after the article has been pulled on over the hips of the wearer.
Figure 3:
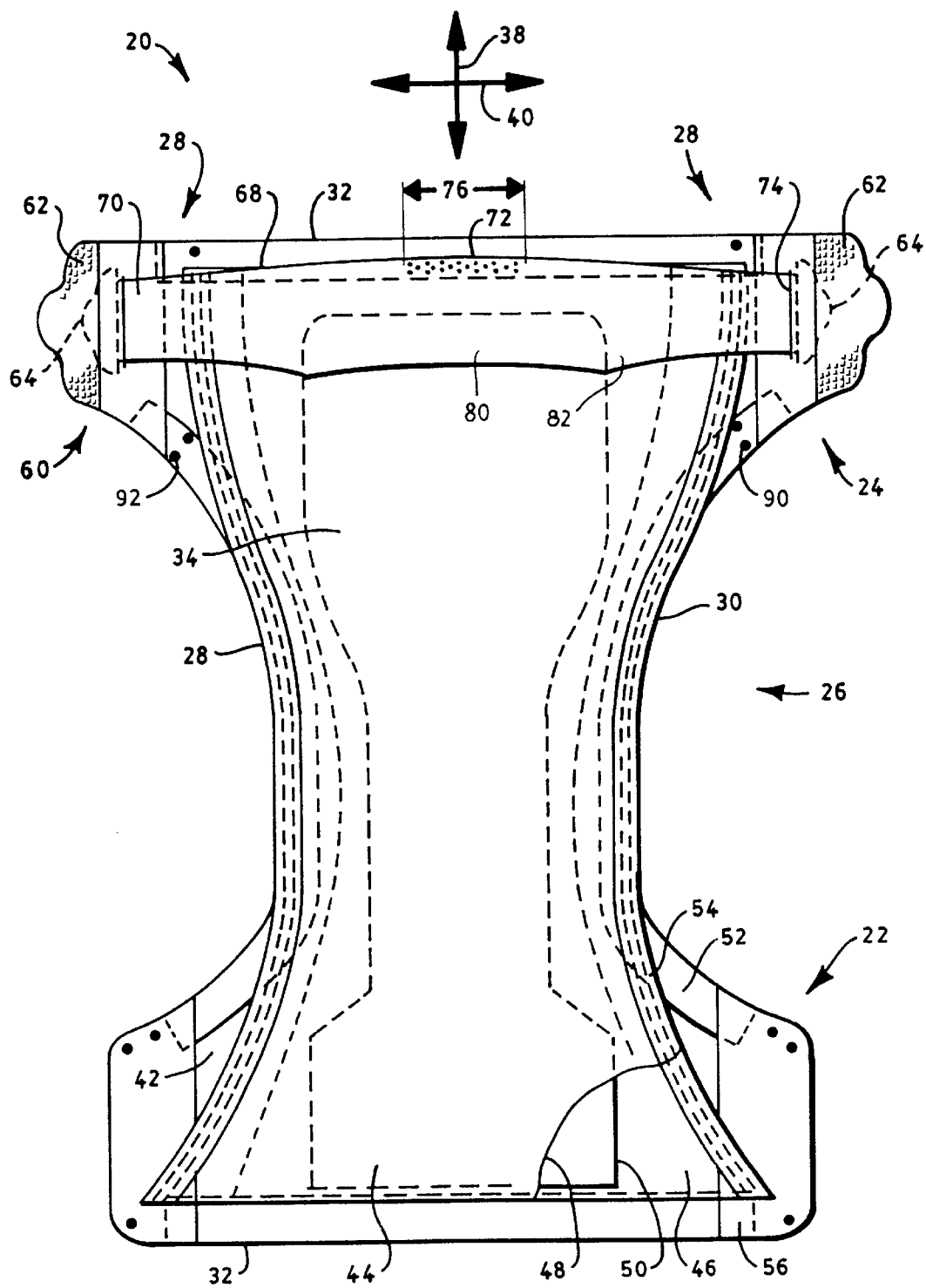
FIG. 3 representatively shows a plan view of the disposable absorbent article of FIG. 1 in an unfastened, stretched and laid flat condition with the surface of the article which contacts the wearer facing the viewer.
Figure 4:
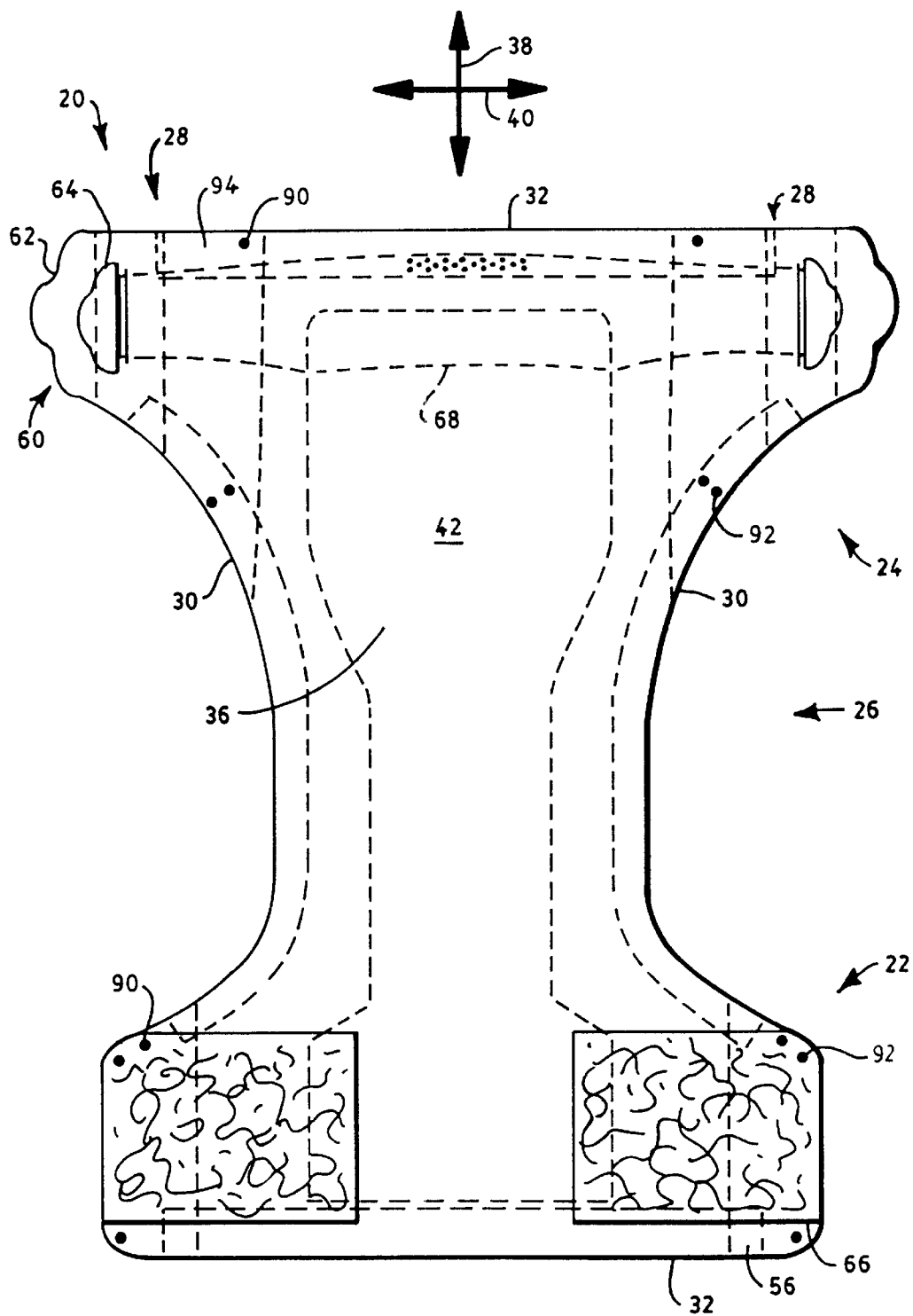
FIG. 4 representatively shows a plan view of the disposable absorbent article of FIG. 1 in an unfastened, stretched and laid flat condition with the surface of the article which contacts the wearer's clothing facing the viewer.

FIGS. 1 and 2 representatively illustrate an example of a prefastened disposable diaper, as generally indicated at 20, according to the present invention. FIGS. 3 and 4 representatively illustrate the diaper of FIG. 1 in an unfastened, stretched and laid flat condition. As representatively illustrated in FIGS. 1–4, the diaper 20 defines a front waist region 22, a back waist region 24, a crotch region 26 which extends between and connects the front and back waist regions 22 and 24 and a pair of laterally opposed ear regions 28 integral with or connected to the back waist region 24. The diaper 20 further defines a pair of laterally opposed side edges 30, a pair of longitudinally opposed waist edges 32, an interior surface 34 which is configured to contact the wearer, an outer surface 36 opposite the interior surface 34, a longitudinal direction 38 and a lateral direction 40.

The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. The ear regions 28 comprise the portions of the diaper which, when worn, are positioned on the side hip areas of the wearer. The laterally opposed side edges 30 of the diaper 20 generally define leg openings which may be curvilinear. The waist edges 32 of the diaper 20 are configured to encircle the waist of the wearer when worn and provide a waist opening when fastened which defines a waist perimeter dimension.

The illustrated diaper 20 includes an outer cover 42, an absorbent chassis 44, and a waistband fastening system 60. The fastening system 60 may include a pair of primary fasteners 62, a pair of secondary fasteners 64 and a pretensioned belt 68. The fastening system 60 may also optionally include a pair of opposed passive side bonds 90 and 92. The absorbent chassis 44 is configured to contain and/or absorb any body exudates discharged from the wearer. Whereas, the outer cover 42 and waistband fastening system 60 are configured to maintain the diaper 20 about the waist of the wearer, conceal the absorbent chassis 44 from view, and provide a garment-like appearance. The diaper 20 may further include leg elastics 52, containment flaps 54 and waist elastics 56 as are known to those skilled in the art. It should be recognized that individual components of the diaper 20 may be optional depending upon the intended use of the diaper 20.

The outer cover 42 of the diaper 20 may suitably be composed of a material which is either liquid permeable or liquid impermeable. Since the absorbent chassis 44 of the different aspects of the present invention is designed to contain the body exudates discharged from the wearer, it is generally not necessary that the outer cover 42 be liquid impermeable. For example, the outer cover 42 may include various woven or nonwoven materials such as spunbond material, meltblown material, cotton material, rayon material or combinations thereof such as a spunbond-meltblown-spunbond (SMS) laminate material.

The outer cover 42 may otherwise be at least partially liquid impermeable to further prevent any leakage of body exudates. For example, a typical outer cover 42 can be manufactured from a thin plastic film or other flexible liquid-impermeable material. In a particular aspect, the outer cover 42 may be formed from a polyethylene film having a thickness of from about 0.012 millimeter (0.5 mil) to about 0.051 millimeter (2.0 mils). The outer cover 42 may also be formed of a woven or nonwoven fibrous web layer which has been totally or partially constructed or treated to impart a desired level of liquid impermeability to selected regions. Further, the outer cover 42 may optionally be composed of a micro-porous "breathable" material which permits vapors to escape from the diaper 20 while still preventing liquid exudates from passing through the outer cover 42. For example, the outer cover 42 may include a microporous film laminated to a nonwoven material such as a spunbond polypropylene material to provide a clothlike feel to the outer cover 42. Still further, the outer cover 42 may be an elasticized material such as a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference.

If it is desired to present the outer cover 42 with a more clothlike feeling, the outer cover 42 may comprise a polyolefin film which may or may not be microporous having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). The outer cover 42 may otherwise be a stretch-thermal laminate (STL) material which includes a film layer positioned between two spunbond layers and which has a basis weight of about 70–75 grams per square meter. The film layer may be composed of meltblown polypropylene fibers and the spunbond layers may be composed of polypropylene fibers. The outer cover 42 may also include bicomponent fibers such as polyethylene/polypropylene bicomponent fibers. Methods of forming such clothlike outer covers are known to those skilled in the art.

The absorbent chassis 44 of the diaper 20 is suitably connected to the outer cover 42 to provide the disposable diaper 20. The absorbent chassis 44 may be connected to the outer cover 42 in manners well known to those skilled in the art. For example, the absorbent chassis 44 may be bonded to the outer cover 42 using adhesive, thermal or ultrasonic bonding techniques known to those skilled in the art. Alternatively, the absorbent chassis 44 may be connected to the outer cover 42 using conventional fasteners such as buttons, hook and loop type fasteners, adhesive tape fasteners, and the like. The other components of the diaper 20 may be suitably connected together using similar means.

Desirably, the absorbent chassis 44 is connected to the outer cover 42 only at or adjacent the waist edges 32 of the outer cover 42 thereby creating a front attached portion, a back attached portion and an unattached portion which extends between and connects the attached portions. The unattached portion of the absorbent chassis 44 remains substantially unattached to the outer cover 42 and is generally configured to fit between the legs of the wearer and at least partially cover the lower torso of the wearer when in use. As a result, the unattached portion is generally the portion of the absorbent chassis 44 which is configured to initially receive the body exudates from the wearer. Thus, the absorbent chassis 44 is connected to the outer cover 42 in such a manner to secure the chassis 44 in place while not adversely restricting the movement of the outer cover 42 in use. Alternatively, the absorbent chassis 44 may be attached to the outer cover 42 along the entire longitudinal length of the absorbent chassis 44 or any portion thereof or along only the outer periphery of the absorbent chassis 44.

As representatively illustrated in FIG. 3, the absorbent chassis 44 according to the present invention may include a backsheet 46, a bodyside liner 48 which is connected to the backsheet 46 in a superposed relation, and an absorbent core 50 which is located between the bodyside liner 48 and the backsheet 46. In alternative configurations wherein the outer cover 42 is at least partially resistant to the flow of liquids therethrough, the backsheet 46 may optionally be omitted from the absorbent chassis 44.

The absorbent chassis 44 is generally conformable and capable of absorbing and retaining body exudates. The absorbent chassis 44 may have any of a number of shapes and sizes. For example, as representatively illustrated in FIG. 3, the absorbent chassis 44 may be rectangular, I-shaped or T-shaped. The size and absorbent capacity of the absorbent chassis 44 should be compatible with the size of the intended wearer and the fluid loading imparted by the intended use of the diaper 20. Typically, it is desirable that the absorbent chassis 44 have an absorbent capacity of at least about 300 grams of urine. It is generally preferred that the absorbent chassis 44 be narrower in the crotch region 26 than in the waist regions 22 and 24. It has been found that the absorbent chassis 44 of the present invention is particularly useful when the width dimension in the crotch region 26 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 44 allows the absorbent chassis 44 to better fit between the legs of the wearer.

The bodyside liner 48 of the absorbent chassis 44, as representatively illustrated in FIG. 3, suitably presents a bodyfacing surface which is intended to be worn adjacent the body of the wearer and is compliant, soft feeling and nonirritating to the wearer's skin. Further, the bodyside liner 48 may be less hydrophilic than the absorbent core 50, to present a relatively dry surface to the wearer, and may be sufficiently porous to be liquid permeable, permitting liquid to readily penetrate through its thickness. A suitable bodyside liner 48 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 48 is suitably employed to help isolate the wearer's skin from fluids held in the absorbent core 50 of the absorbent chassis 44.

Various woven and nonwoven fabrics can be used for the bodyside liner 48. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 48 comprises a nonwoven, spunbond, polypropylene fabric composed of about 2.8–3.2 denier fibers formed into a web having a basis weight of about 22 grams per square meter and a density of about 0.06 grams per cubic centimeter.

The backsheet 46 of the absorbent chassis 44, as representatively illustrated in FIG. 3, may suitably be composed of a material which is either liquid permeable or liquid impermeable. It is generally preferred that the backsheet 46 be formed from a material which is substantially impermeable to fluids. A typical backsheet can be manufactured from a thin plastic film or other flexible liquid-impermeable material. For example, the backsheet 46 may be formed from a polyethylene film having a thickness of from about 0.012 millimeter (0.5 mil) to about 0.051 millimeter (2.0 mils). The backsheet 46 may also comprise a film layer having a nonwoven web laminated to the outer surface thereof, such as a spunbond web of polyolefin fibers. The backsheet 46 may also be constructed of a material which is similar to the material described above as being suitable for the outer cover 42. Further, the backsheet 46 may be formed of a woven or nonwoven fibrous web layer which has been totally or partially constructed or treated to impart a desired level of liquid impermeability to selected regions that are adjacent or proximate the absorbent core 50. Still further, the backsheet 46 may optionally be composed of a micro-porous "breathable" material which permits vapors to escape from the absorbent core 50 while still preventing liquid exudates from passing through the backsheet 46. For example, the backsheet 46 may include a breathable polyethylene film material commercially available from Exxon Chemical Patents, Incorporated, a business having offices located in Linden, N.J., under the trade designation EXXAIRE. In such a configuration, it is desirable that the outer cover 42 also comprise a breathable material.

The bodyside liner 48 and backsheet 46 are generally adhered to one another so as to form a pocket in which the absorbent core 50 is located to provide the absorbent chassis 44. The bodyside liner 48 and backsheet 46 may be adhered directly to each other around the outer periphery of the absorbent chassis 44 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 48 to the backsheet 46. It should be noted that both the bodyside liner 48 and the backsheet 46 need not extend completely to the outer periphery of the absorbent chassis 44. For example, the backsheet 46 may extend to the outer periphery of the absorbent chassis 44 while the bodyside liner 48 may be attached to the backsheet 46 inboard of the outer periphery of the absorbent chassis 44, or more towards the longitudinal centerline 38 of the diaper 20. In alternative configurations, especially wherein the backsheet 46 is omitted, the bodyside liner 48 may be suitably adhered directly to the absorbent core 50 or to the outer cover 42.

The absorbent core 50, as representatively illustrated in FIG. 3, is positioned between the bodyside liner 48 and the backsheet 46 to form the absorbent chassis 44. The absorbent core 50 is desirably conformable and capable of absorbing and retaining body exudates. The absorbent core 50 may have any of a number of shapes and sizes. For example, the absorbent core may be rectangular, I-shaped or T-shaped. It is generally preferred that the absorbent core 50 be narrower in the crotch region 26. The size of the absorbent core 50 should be compatible with the size of the intended wearer and the desired absorbent capacity of the absorbent chassis 44.

The absorbent core 50 of the absorbent chassis 44 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 50 may also comprise selected blends of the various types of fibers mentioned above.

In a particular aspect of the invention, the absorbent core 50 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 50 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 50 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va. Other suitable high-absorbency materials may include superabsorbent polymers which are commercially available from Dow Chemical Corp., a business having offices in Midland, Mich.

As a general rule, the high-absorbency material is present in the absorbent core 50 of the present invention in an amount of from about 5 to about 95 weight percent and desirably from about 10 to about 60 weight percent based on the total weight of the absorbent core 50. The distribution of the high-absorbency material within the different portions of the absorbent core 50 can vary depending upon the intended end use of the absorbent core 50.

As representatively illustrated in FIG. 3, the absorbent chassis 44 of the disposable diaper 20 may include a pair of containment flaps 54 which are configured to provide a barrier to the lateral flow of body exudates. The containment flaps 54 may be located along the laterally opposed side edges of the absorbent chassis 44. Each containment flap 54 typically defines an unattached edge which is configured to maintain an upright, perpendicular configuration in at least the crotch region 26 of the diaper 20 to form a seal against the wearer's body. The containment flaps 54 may extend longitudinally along the entire length of the absorbent chassis 44 or may only extend partially along the length of the absorbent chassis 44. When the containment flaps 54 are shorter in length than the absorbent chassis 44, the containment flaps 54 can be selectively positioned anywhere along the side edges of the absorbent chassis 44. In a particular aspect of the invention, the containment flaps 54 extend along the entire length of the absorbent chassis 44 to better contain the body exudates.

Such containment flaps 54 are generally well known to those skilled in the art. For example, suitable constructions and arrangements for containment flaps 54 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edges 32 and side edges 30 of the diaper 20 to further prevent the leakage of body exudates and support the absorbent chassis 44. For example, as representatively illustrated in FIG. 3, the diaper 20 of the present invention may include a pair of leg elastic members 52 which are connected to the laterally opposed side edges 30 in the crotch region 26 of the diaper 20 and a waist elastic member 56 which is connected to the waist edge 32 of the diaper 20 in the back waist region 24. The leg elastics 52 and waist elastic 56 are generally adapted to fit about the legs and waist of a wearer in use to maintain a positive, contacting relationship with the wearer to effectively reduce or eliminate the leakage of body exudates from the diaper 20.

Materials suitable for use as the leg elastics 52 and waist elastic 56 are well known to those skilled in the art. Exemplary of such materials are sheets or strands or ribbons of a polymeric, elastomeric material which are adhered to the edges 30 and 32 of the diaper 20 in a stretched position, or which are attached to the edges 30 and 32 while the edges are pleated, such that elastic constrictive forces are imparted to the edges 30 and 32. The leg elastics may also include such materials as polyurethane, synthetic and natural rubber, elastic adhesives and the like. In a particular aspect of the invention, the elastics may be composed of individual strands of 620 decitex LYCRA which are commercially available from E. I. DuPont de Nemours Co. When individual strands of elastic are used, the waist and leg elastics may include any suitable number of elastic strands to provide containment of the body exudates. For example, the leg elastics 52 may include from about 1 to about 10 elastic strands. The elastics 52 and 56 may be elongated prior to being attached to the diaper 20. For example, the elastics 52 and 56 may be elongated at least about 150 percent and desirably from about 200 to about 500 percent before being attached such that the elastics gather the edges 30 and 32 of the diaper 20 when relaxed. The elastics 52 and 56 may be joined to the diaper 20 by any means known to those skilled in the art. For example, adhesive, thermal or ultrasonic bonding techniques or a combination thereof may be used to join the elastics to the edges of the diaper 20. A suitable adhesive includes Findley H-2096 hot melt adhesive which is commercially available from Findley Adhesives, Inc.

The absorbent article of the different aspects of the present invention further includes an adjustable, pretensioned waistband fastening system 60 for securing the absorbent article about the waist of the wearer. The waistband fastening system includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer.

Examples of diapers which include waistband fastening systems are described in U.S. patent application Ser. No. 08/907,585 entitled "A WAISTBAND FASTENER FOR DISPOSABLE ABSORBENT ARTICLES" and filed Aug. 8, 1997 in the name of J. D. Suprise, and U.S. patent application Ser. No. 09/100,681 entitled "ABSORBENT ARTICLES HAVING BELT LOOPS AND AN ADJUSTABLE BELT" and filed Jun. 19, 1998 in the name of Blenke et al., the disclosures of which are hereby incorporated by reference. As representatively illustrated in FIGS. 1–4, the adjustable, pretensioned waistband fastening system 60 of the present invention may include a pair of primary fasteners 62 which are located on the side edges 30 of the diaper 20 in the back waist region 24 of the diaper 20. In such a configuration, the primary fasteners 62 are configured to encircle the hips of the wearer and engage the outer surface 36 of the front waist region 22 of the diaper 20 to maintain the diaper 20 on the wearer. Alternatively, the primary fasteners 62 may be located on the front waist region 22 and may be configured to releasably engage the outer surface 36 of the back waist region 24 of the diaper 20.

Desirably, the primary fasteners 62 are releasably engageable directly with the outer surface of the outer cover 42 of the diaper 20 to provide improved ease of fastening. Alternatively, as representatively illustrated in FIG. 4, the disposable diaper 20 of the present invention may further include an attachment panel 66 located on the outer cover 42 in one of the waist regions 22 and 24 of the diaper 20. In such a configuration, the primary fasteners 62 are releasably engageable with the attachment panel 66 to maintain the diaper 20 about the waist of the wearer. When the primary fasteners 62 are releasably engaged, the side edges 30 of the diaper 20 define leg openings which are configured to encircle the legs of the wearer and the waist edges 32 define a waist opening which is configured to encircle the waist of the wearer. As illustrated in FIG. 4, the attachment panel 66 may include two separate panels located along the opposite side edges in one of the waist regions 22 and 24 of the diaper 20. Alternatively, the attachment panel 66 may include a single piece of material which extends substantially across the respective waist region of the diaper 20.

In the different aspects of the present invention, the primary fasteners 62 are releasably engaged with the outer surface of the opposite waist region 22 and 24 of the diaper 20 before the diaper 20 is placed on the wearer to provide a prefastened diaper. In such a configuration, the prefastened diaper 20 can be pulled on or off over the legs and hips of the wearer. If the diaper 20 becomes soiled during use, the primary fasteners 62 can be disengaged to easily remove the diaper 20 from the waist of the wearer with reduced risk of undesirably soiling the clothes or legs of the wearer. Thus, in such a configuration, the diaper 20 of the different aspects of the present invention can be configured to be pulled on or off over the hips of the wearer such as conventional training pants and can be readily removed by disengaging the fasteners similar to conventional diaper articles.

The adjustable, pretensioned waistband fastening system 60 of the absorbent article of the present invention further includes a waistband adjusting mechanism located in one of the waist regions 22 and 24, such as belt 68, which is configured to exert a pretensioning force on the waist regions and further conform the waist regions 22 and 24 of the diaper 20 to the waist of the wearer after the diaper 20 has been pulled on over the hips of the wearer. The belt 68 includes a pair of laterally opposed end portions 70 and at least one secondary fastener 64 connected to one of the opposed end portions 70. The belt 68 is configured to provide a pretension on the one waist region and is capable of elongating such that the secondary fastener 64 can be releasably engaged with the opposite waist region to further conform the waist regions to the waist of the wearer when the primary fasteners 62 are releasably engaged. The primary fasteners 62 are also capable of being reengaged after the diaper is pulled on to further conform the waist regions of the diaper to the waist of the wearer.

In the illustrated embodiments, the diaper 20 includes a pair of secondary fasteners 64 connected to the opposed end portions 70 of the belt 68. In such a configuration, both end portions 70 of the belt 68 are configured to encircle the hips of the wearer such that the secondary fasteners 64 can releasably engage the opposite waist region to provide the improved fit of the diaper on the wearer after the diaper 20 has been pulled on over the legs and hips of the wearer. In a particular embodiment, the secondary fasteners 64 and belt 68 may be located in the back waist region 24 of the diaper 20. In such a configuration, the secondary fasteners 64 are configured to encircle the hips of the wearer and engage the outer surface 36 of the front waist region 22 of the diaper 20 to maintain the diaper 20 on the wearer. Alternatively, the secondary fasteners 64 and belt 68 may be located in the front waist region 22 and may be configured to releasably engage the outer surface 36 of the back waist region 24 of the diaper 20. If only one secondary fastener 64 is used (not illustrated), the end portion 70 of the belt 68 which is not attached to the secondary fastener 64 may be attached to one of the other components of the diaper 20 such as the outer cover 42.

Desirably, the secondary fasteners 64 are releasably engageable directly with the outer surface of the outer cover 42 of the diaper 20 to provide improved ease of fastening. Alternatively, as described above and representatively illustrated in FIGS. 1–4, the diaper 20 of the present invention may further include an attachment panel 66 located on the outer cover 42 in one of the waist regions 22 and 24 of the diaper 20. In such a configuration, the secondary fasteners 64 may also be releasably engageable with the attachment panel 66 to maintain the diaper 20 about the waist of the wearer.

The use of the combination of the secondary fasteners 64 and the belt 68 has been found to be particularly desirable when the primary fasteners 62 are releasably engaged with the respective waist region of the diaper 20 to provide a prefastened diaper, similar to conventional training pants. In such a configuration, the waist opening of the diaper 20 when the primary fasteners 62 are engaged must be sufficient to allow the prefastened diaper to be pulled over the hips of the wearer. However, the circumference of the waist of the wearer is typically less than the circumference around the hips and buttocks of the wearer. Thus, the waist opening of the prefastened diaper may not conform to the waist of the wearer which may undesirably result in leaks.

The secondary fastener 64 and belt 68 of the diaper 20 of the present invention are configured to conform the waist regions of the diaper 20 to the wearer by reducing the waist perimeter dimension of the diaper 20 after the prefastened diaper is pulled on the wearer. In particular, the belt 68 is configured to position itself above and be supported by the upper portion of the hips of the wearer and dip below the stomach or belly of the wearer to provide a close, conforming fit about the waist. Thus, the care giver is not required to reposition the primary fasteners 62 to conform the waist regions 22 and 24 to the waist of the wearer. As a result, when the diaper 20 is to be removed from the wearer, the care giver may simply disengage the secondary fasteners 64 if necessary and pull the prefastened diaper down over the hips and legs of the wearer without having to reposition or disengage the primary fasteners 62. Alternatively, the care giver may also disengage the primary fasteners 64 and 62 to remove the diaper in a manner similar to conventional diapers.

Thus, the adjustable, pretensioned waistband fastening system 60 of the present invention is intended to maintain the diaper 20 in a close conforming fit about the waist of the wearer to reduce the leakage of body exudates when in use. The primary fasteners 62 are intended to maintain the front and back waist regions 22 and 24 of the diaper 20 connected in such a manner that the diaper 20 can be pulled on or off over the hips of the wearer after the secondary fasteners 64 have been disengaged. The secondary fasteners 64 and belt 68 are configured to conform the waist regions of the diaper 20 to the wearer by reducing the waist perimeter dimension of the diaper 20 after the prefastened diaper is pulled on the wearer. The secondary fasteners 64 may also be selectively disengaged to facilitate inspection of the diaper 20 to determine if it has been soiled. The primary fasteners 62 can also provide a "childproofing function" by maintaining the diaper 20 at least partially secured about the waist of the wearer if the wearer disengages the secondary fasteners 64.

The combination of the secondary fasteners 64 and belt 68 may also provide improved fit when the diaper 20 is applied from an unfastened configuration similar to conventional diapers. For example, upon the initial fastening about the wearer, the primary fasteners 62 may be difficult to locate correctly due to the activity of the wearer. Thus, in such situations, the secondary fasteners 64 and belt 68 can be used to provide a better conforming fit after the primary fasteners 62 have been engaged.

Suitable fasteners are well known to those skilled in the art and can include adhesive tape tab fasteners, cohesives, magnetics, hook and loop fasteners, mushroom fasteners, snaps, pins, belts and the like, and combinations thereof. For example, as representatively illustrated in FIG. 3, the primary fasteners 62 and secondary fasteners 64 may be hook type fasteners and the outer cover 42 or attachment panel 66 may be configured to function as a complimentary loop type fastener. Desirably, the fasteners 62 and 64 are hook type fasteners which are releasably engageable directly with the outer cover 42. Such an arrangement provides the ability to vary the size of the waist opening in very small increments over a wide range to fit the waist of the wearer. The fasteners may have any shape and size which provides the desired fastening of the diaper 20 about the waist of the wearer. It is further desirable that the outer surface of the secondary fasteners 64 provide a visual cue to the care giver as to their location. For example, in one embodiment, the secondary fasteners 64 are of a different color than the outer surface of the diaper 20 to enable the care giver to easily determine the location of the secondary fasteners 64.

In the illustrated embodiments, the primary fasteners 62 are attached directly to the side edges 30 of the diaper 20 in one of the waist regions 22 and 24. The primary fasteners 62 may be adhered to the side edges 30 by any means known to those skilled in the art such as adhesive bonds, sonic bonds, thermal bonds and the like and combinations thereof.

To provide the improved fit about the waist of the wearer without adversely affecting the appearance of the outer cover 42 of the diaper 20, the majority of the length of the belt 68 desirably is positioned between the wearer and the outer cover such as along the interior surface 34 of the diaper 20 in the respective waist region 22 and 24. In such a configuration as representatively illustrated in FIG. 3, the diaper 20 may further include a pair of slots 74 through which the end portions 70 of the belt 68 slidably extend. Thus, in the illustrated embodiment, the end portions 70 of the belt 68 and the secondary fasteners 64 are located on the outer surface 36 of the diaper and the remaining portion of the belt 68 extends through to and along the interior surface 34 of the diaper 20 between the diaper and the wearer. As illustrated, the secondary fasteners 64 are desirably configured to releasably engage the outer surface 36 of the diaper 20 adjacent the slots 74 for improved control and ease of fastening.

The slots 74 may be provided by any means known to those skilled in the art. For example, the slots 74 may be provided by cutting the diaper 20 after it has been assembled together. Alternatively, the slots 74 may be provided by adding a segment of material to the side edges 30 of the diaper 20 which extends laterally outward from the side edges 30 while only attaching the segment of material to the side edges at its longitudinal ends to create a belt loop type arrangement. In such a configuration, the segment of material provides a slot between the side edge of the diaper and the segment of material for improved manufacturability.

A portion of the belt 68 between the wearer and the outer cover 42 may be secured to an interior surface of the diaper 20 to provide an attached portion 72. The attached portion 72 of the belt 68 may be secured to the interior surface of the diaper using methods known to those skilled in the art such as adhesive, sonic or thermal bonding. Desirably, the attached portion 72 defines a total attached length 76 as illustrated in FIG. 3 which is less than about 75 percent and more desirably less than about 50 percent of the total length of the belt 68. Such an attached length 76 provides sufficient securement of the belt to the diaper 20 without adversely affecting the ability of the belt to conform to the waist of the wearer to provide the improved fit without bunching or adversely affecting the appearance of the outer cover. The attached portion 72 can be in the center of the diaper 30 as illustrated or in another alternative location or locations. For example, the belt 68 may selectively define two laterally opposed attached portions.

In alternative configurations, the belt 68 need not extend all the way through the diaper 20 to the interior surface 34. For example, the majority of the belt 68 may extend between the outer cover 42 and the absorbent chassis 44 or between any of the components of the absorbent chassis to further conceal the belt 68.

Figure 6:
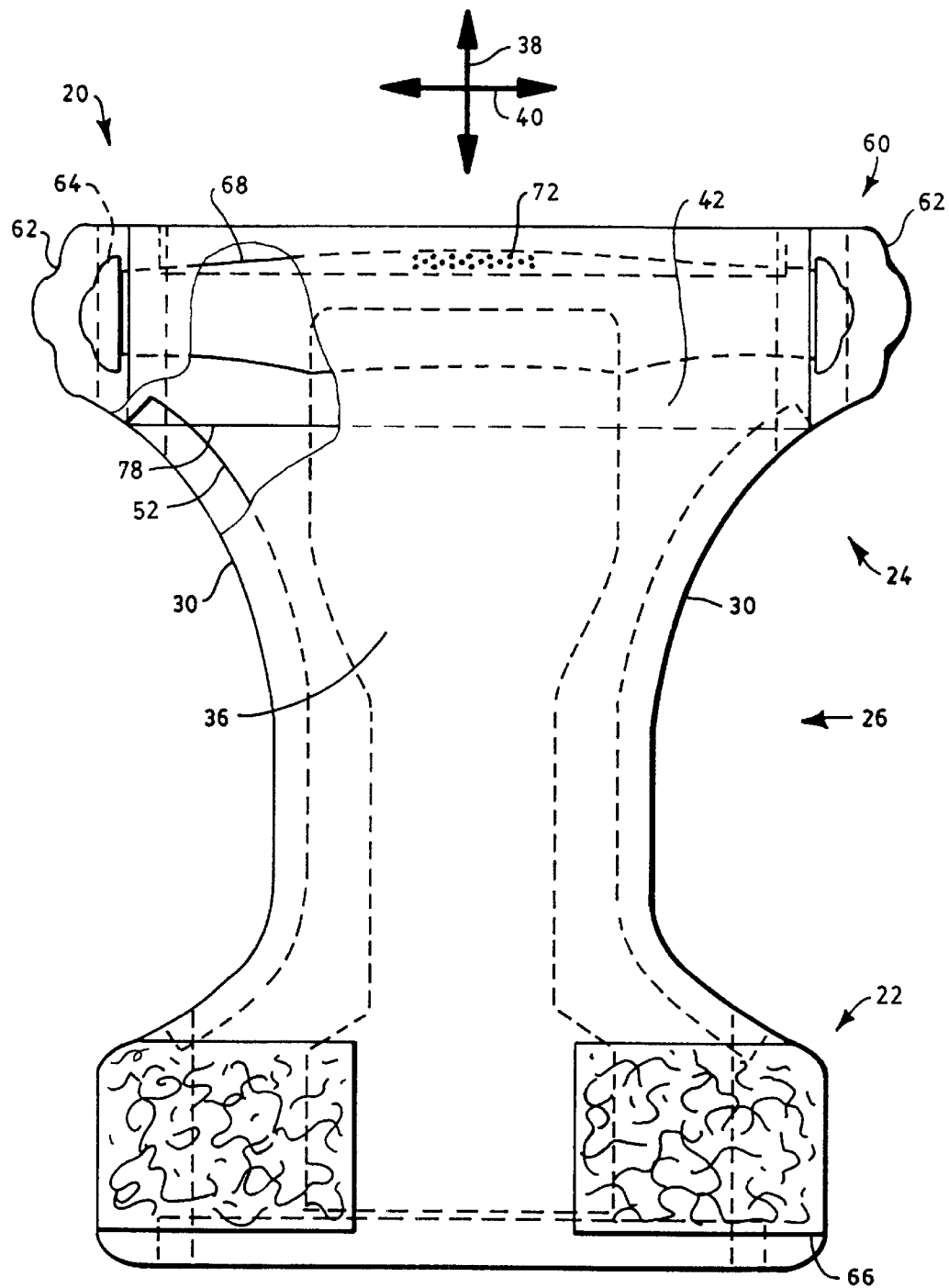
FIG. 6 representatively shows a plan view of another example of a disposable absorbent article of the present invention in an unfastened, stretched and laid flat condition with the surface of the article which contacts the wearer's clothing facing the viewer and with portions of the article cut away to more clearly illustrate the underlying features.
Figure 7:
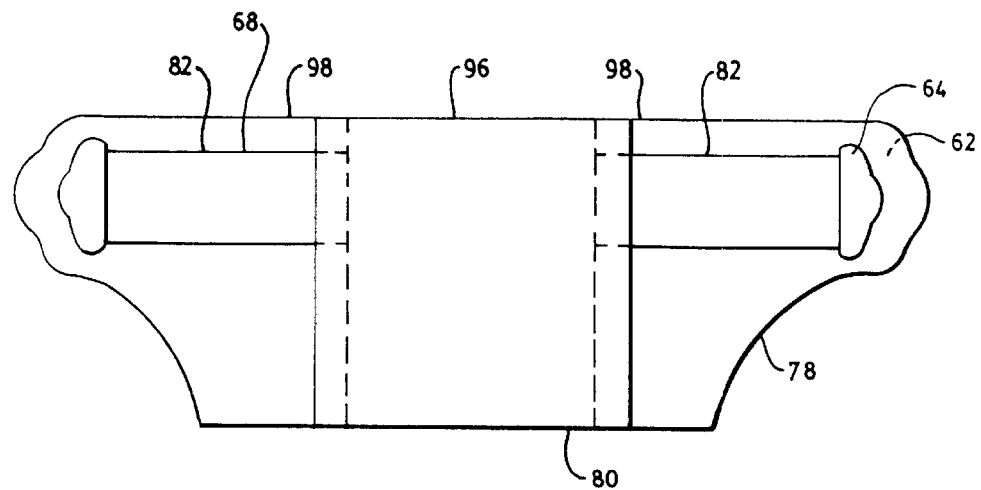
FIG. 7 representatively shows a plan view of the pretensioned, adjustable waistband fastening system of the absorbent article of FIG. 6.
Figure 8:
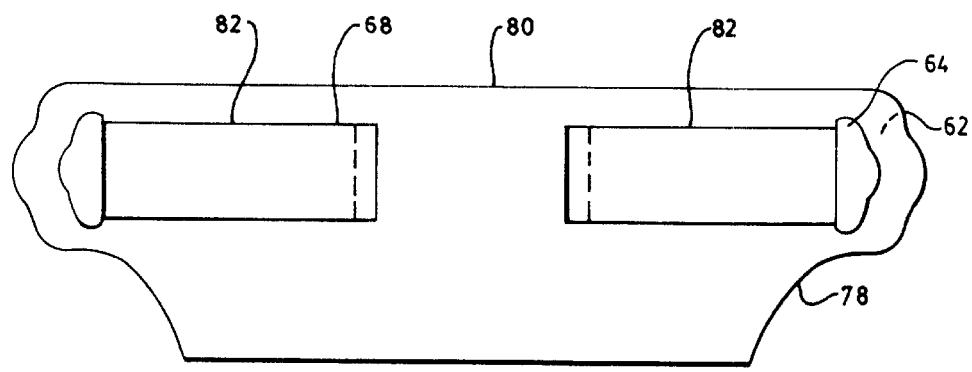
FIG. 8 representatively shows a plan view of another alternative configuration of the pretensioned, adjustable waistband fastening system of the absorbent article of FIG. 6.

To provide improved manufacturability, the fastening system 60 on the diaper 20 of the present invention may include a carrier panel 78, as representatively illustrated in FIGS. 6–8, to facilitate incorporation of the belt 68 and secondary fasteners 64 into the diaper 20. For example, the belt 68 may be attached to the carrier panel 78 by releasable engaging the secondary fasteners 64 on the opposed end portions 70 of the belt 68 to the carrier panel 78. In addition, portions of the belt 68 may be bonded directly to the carrier panel 78 using conventional methods such as thermal, adhesive, ultrasonic bonds and the like or combinations thereof. The illustrated carrier panel 78 and belt 68 can then be incorporated into the diaper 20 by bonding the carrier panel 78 in a facing relationship to the outer cover 42 using similar methods. The belt 68 on the illustrated carrier panels 78 is placed between the outer cover 42 and the carrier panel 78 before the carrier panel 78 is bonded to the outer cover 42.

In such a configuration, the outer cover 42 may define a width which is less than the length of the belt 68 at this location such that at least a portion of the secondary fasteners 64 are not concealed by the outer cover 42. In this configuration, the primary fasteners 62 may also be attached to the surface of the opposed side edges of the carrier panel 78 opposite the surface to which the belt 68 is attached. Thus, in such an arrangement, the waistband fastening system 60 may be provided separately and then incorporated into the absorbent article for reduced manufacturing complexity and improved efficiency. Further methods of providing such a carrier panel are described in U.S. patent application Ser. No. 09/100,547 filed Jun. 19, 1998 in the name of Blenke et al. and entitled "ABSORBENT ARTICLES HAVING A STRETCH BAND AND METHODS OF MAKING THE SAME", the disclosure of which is hereby incorporated by reference.

Materials suitable for the belt 68 and carrier panel 78 include some of those materials described above as being suitable for the outer cover 42. For example, the belt 68 may comprise an elastic material which is capable of elongating at least about 50 percent and more desirably at least about 100 percent to provide improved fit about the waist of the wearer. For example, the belt 68 may comprise a neck bonded laminate material which includes a KRATON film material commercially available from the Dow Chemical Company, a business having offices located in Midland, Mich. The belt 68 may otherwise be made of a latent elastic material which may be elastically activated after the diaper 20 is constructed and before it is worn. In a particular embodiment, the belt 68 is made of a latent elastic material as described in U.S. patent application Ser. No. 08/854,934 filed May 13, 1997 and entitled "IMPROVED COMPOSITE ELASTIC MATERIAL AND PROCESS FOR PRODUCING THE SAME", the disclosure of which is hereby incorporated by reference. Alternatively and in a desirable configuration as discussed below, the belt 68 may include portions which include elastic material and portions which include latent material.

The belt 68 of the different aspects of the present invention desirably maintains at least some pretension on the waist region 22 or 24 to which it is attached. The belt 68 can provide such pretension on the waist region in a variety of ways. For example, the belt 68 may be made of an elastic material and the belt 68 may be stretched before being applied to the waist region 22 or 24 such that upon release of the stretching force the belt 68 retracts thereby providing the pretension on the waist region.

Alternatively, the belt 68 or at least portions of the belt 68 may include latent materials which can be applied in a latent state and activated as desired to provide the desired pretension on the waist region. For example, the belt 68 may include a latent material which is activated after the manufacture if the article is complete or at least near completion to provide improved manufacturability.

If the belt 68 is made solely from an elastic material as described above, the belt 68 must be elongated before being attached to the article to provide the desired pretension on the waist region of the article. However, such pretension can be difficult to control as the absorbent article is further manufactured which can result in reduced quality. In particular, such pretension will cause the continuous web of absorbent articles to undesirably neck down.

Thus, to reduce this tendency to neck down and provide improved manufacturability, the belt 68 desirably exerts the pretension force on the article only after the article is substantially complete. The use of latent materials in at least a portion of the belt 68 can provide a solution to this problem. For example, as representatively illustrated In FIGS. 5A–5C, the belt 68 may include a latent segment 80. In such a configuration, the belt 68 can be attached to the diaper 20 in a nonactivated, non-elongated, relaxed condition such that it does not adversely affect the product web. As such the belt 68 defines a first length 84 as representatively illustrated in FIG. 5A.

After the diaper 20 is assembled together, the diaper may be subjected to a source of energy such as heat or microwave energy to activate the latent segment 80 in the belt 68 thereby causing it to reduce in length and pretensioning the waist region 22 or 24 to which it is attached. An example of the belt 68 illustrated in FIG. 5A in such an activated, pretensioned state is representatively illustrated in FIG. 5B. As illustrated in FIG. 5B, the activated belt defines a second length 86 which is less than the first length 84 of the belt 68 in it's unactivated state. In such a configuration, the second length 86 of the belt 68 in it's activated or pretensioned state as shown in FIG. 5B is desirably less than about 90 percent, more desirably less than about 70 percent and even more desirably less than about 50 percent of it's first length 84 in an unstretched and inactivated or non-pretensioned state shown in FIG. 5A to provide a close conforming fit after the diaper 20 is pulled on over the hips of the wearer for improved performance.

Suitable latent materials for the latent segment 80 of the belt 68 are known to those skilled in the art and described above. For example, the latent segment 80 of the belt 68 may include a latent nonelastic material such as a latent film material commercially available from Huntsman Packaging, a business having offices located in Chippewa Falls, Wis. under the trade designation SO-19-62-SHRINK. Alternatively, the latent segment 80 may include a latent elastic material which is capable of elongating after it has been activated such as a latent elastic material commercially available from Exxon Chemical Company a business having offices located in Houston, Tex. under the trade designation EXX-601.

As discussed above, the belt 68 also must be capable of elongating beyond its unstretched, non-pretensioned state 84 such that the belt 68 and secondary fasteners 64 can further conform the waist regions of the article to the wearer's body. Desirably, the belt 68 is elongatable to a third length 88 as shown in FIG. 5C which is at least about 105 percent, more desirably at least about 112 percent and even more desirably at least about 130 percent of it's first length 84 in an unstretched and inactivated or non-pretensioned state as shown in FIG. 5A to allow the caregiver to further adjust the waist of the diaper 20 to provide a close, conforming fit to the wearer.

Suitable materials which provide such elongation are known to those skilled in the art. For example, the belt 68 may be made completely from a latent elastic material such as that described above. However, in general, such latent elastic materials can be costly and do not always provide the desired levels of elongation. Accordingly, the belt 68 of the article of the different aspects of the present invention desirably includes at least one elastic segment in addition to the latent segment 80. For example, as representatively illustrated in FIGS. 5A–5C, the belt 68 may include two laterally opposed elastic segments 82 with the latent segment 80 positioned in between. In such a configuration, the secondary fasteners 64 are attached to the elastic segments 82.

Suitable materials for the elastic segment 82 are well known to those skilled in the art and described above. When the belt includes such an elastic segment, it is not necessary that the latent segment have any elastic properties after it is activated which can desirably lead to the use of lower cost latent materials.

Figure 5A:
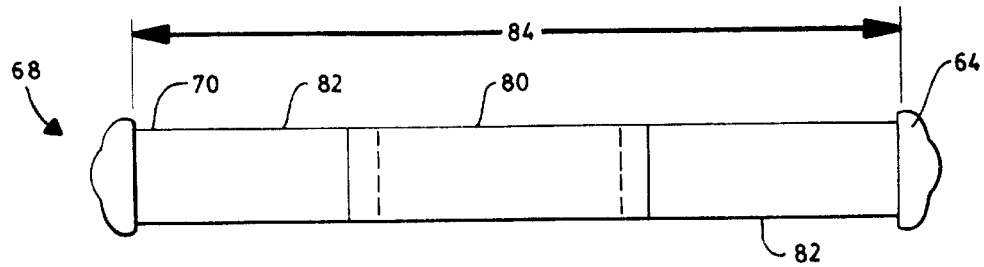
FIG. 5A representatively shows a plan view of an example of an adjustable waistband of the absorbent article of the present invention in an untensioned, non-activated condition as it is applied to the absorbent article.
Figure 5B:
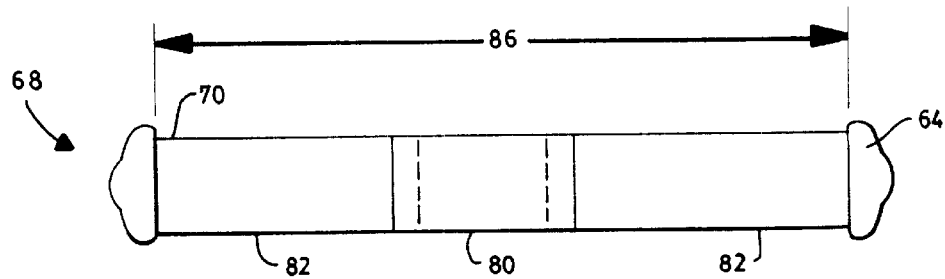
FIG. 5B representatively shows a plan view of the adjustable waistband of FIG. 5A in an activated condition.
Figure 5C:
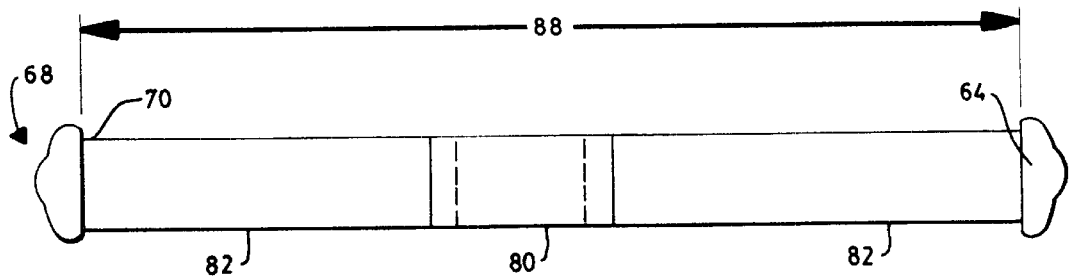
FIG. 5C representatively shows a plan view of the adjustable waistband of FIG. 5A in an activated and elongated condition.

Thus, in a particular embodiment as illustrated in FIGS. 5A–5C, the belt 68 of the present invention includes a latent segment 80 between two elastic segments 82. In such embodiment, the latent segment 80 includes a latent non-elastic film material commercially available from Huntsman Packaging under the trade designation SO-19-62-SHRINK and the elastic segments 82 include a neck bonded laminate material manufactured by Kimberly-Clark Corporation a business having offices located in Neenah, Wis.

The segments 80 and 82 can be joined together by suitable methods such as adhesive, thermal, ultrasonic bonds and the like and combinations thereof. The lengths of the different segments 80 and 82 are not critical and can be adjusted depending upon the desired pretension and elongation properties and the properties of the particular materials selected to provide the segments 80 and 82.

In alternative embodiments as representatively illustrated in FIGS. 7 and 8, the carrier panel 78 may be used to provide the latent segment of the belt 68. For example, as illustrated in FIG. 7, the carrier panel 78 may include a central latent portion 96 between opposed outer portions 98. In such a configuration, the elastic segments 82 of the belt 68 are attached to the latent portion 96 of the carrier panel 78 at laterally spaced apart locations and the latent portion 96 of the carrier panel 78 thereby provides the latent segment of the belt 68. Alternatively, as representatively illustrated in FIG. 8, the carrier panel 78 may be made entirely from a latent material. In such a configuration, the elastic segments 82 of the belt 68 are attached to the latent carrier panel 78 at laterally spaced apart locations and the portion of the carrier panel 78 between the elastic segments 82 provides the latent segment of the belt 68.

The belt 68 may define any length and width which provide the desired improved fastening and fit about the wearer. For example, the belt 68 may define a length which is from about 7 to about 35 centimeters and a width which is from about 1 to about 10 centimeters in an unstretched, non-activated, relaxed state. As discussed above, the belt 68 desirably defines an activated length which is slightly less than the width of the diaper 20 at the respective waist region such that the belt 68 exerts a pretension on the respective waist region.

The prefastened absorbent article of the different aspects of the present invention may further include a pair of passive side bonds for improved reliability of maintaining the article in the prefastened condition particularly when it is being pulled on or off over the hips of the wearer. For example, as representatively illustrated in FIGS. 1–4, the diaper 20 may include a pair of passive side bonds 90 and 92 which releasably connect an overlapped portion 94 of the back waist region 24 or the opposed ear regions 28 to the front waist region 22 of the diaper 20. In such a configuration, the passive side bonds 90 and 92 assist the fastening system 60 in maintaining the diaper 20 in a prefastened condition as the diaper 20 is pulled up or down over the hips of the wearer. Moreover, the passive side bonds 90 and 92 prevent movement and shifting of the waist regions 22 and 24 and ear regions 28 relative to each other for improved fit and performance. The passive side bonds 90 and 92 also provide improved hip coverage and prevent rollover or folding of the side edges 30 and waist edges 32 of the prefastened diaper 20 as it is pulled over the wearers hips. Such prevention of rollovers and foldovers can reduce the level of contact between the fasteners and the skin of the wearer which can desirably result in reduced skin irritation and redness.

The passive side bonds 90 and 92 can be provided by any type of bonding such as thermal, adhesive, ultrasonic, cohesive bonding and the like and combinations thereof as are well known to those skilled in the art. The passive side bonds 90 and 92 may otherwise be provided by suitable fasteners as are known to those skilled in the art and described above as being suitable for use as the primary fasteners 62. The passive side bonds 90 and 92 may be discrete point bonds, dashed lines, continuous lines, discontinuous lines and the like or combinations thereof. Moreover, the side bonds 90 and 92 may have any shape such as circular, square, triangular and the like. In a particular embodiment, the passive side bonds 90 and 92 are ultrasonic point bonds for improved manufacturing efficiency.

Suitable configurations of the passive side bonds 90 and 92 and methods of incorporating them are described in copending U.S. patent application Ser. No. 09/100,574, entitled "DISPOSABLE ABSORBENT ARTICLES HAVING PASSIVE SIDE BONDS AND ADJUSTABLE FASTENING SYSTEMS" filed on Jun. 19, 1998 in the name of Elsberg and U.S. patent application Ser. No. 09/100,911 entitled "METHOD OF MAKING PREFASTENED DISPOSABLE ABSORBENT ARTICLES" filed Jun. 19, 1998 in the name of Elsberg et al., the disclosures of which is hereby incorporated by reference.

In another aspect, the present invention provides a package of the prefastened disposable diapers described above. The package includes a container such as, for example, a plastic bag, and a plurality of prefastened disposable diapers. As described above, the prefastened diaper 20 includes a pair of primary fasteners 62 which are releasably engaged to secure the waist regions of the article together to provide the prefastened configuration. Such a package provides diapers which can be reliably pulled on over the legs of the wearer and which can be easily removed from the waist of the wearer after they have been soiled.

The different aspects of the present invention can advantageously provide a prefastened disposable absorbent article which includes an adjustable, pretensioned waistband fastening system. The primary fasteners of the fastening system are prefastened to releasably engage the front and back waist portions to allow the absorbent article to be pulled up or down over the hips of the wearer such as conventional training pants. Moreover, the primary fasteners of the fastening system can be used to releasably engage and adjust the front and back waist portions of the absorbent article to maintain the absorbent article about the waist of the wearer after the article has been pulled on in a similar manner to conventional diapers. Further, the pretension on the waist band and the elongation supplied by the belt and secondary fasteners of the fastening system provide a close, conforming fit to the wearer without requiring that the primary fasteners be disengaged and refastened.

As a result, the absorbent articles of the present invention are designed to conform to the body of the wearer to effectively contain bodily exudates while still being capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

What is claimed is:

1. A prefastened disposable absorbent article which defines an absorbent, a front waist region, a back waist region, a crotch region which extends between and connects said waist regions and a pair of opposed side edges wherein said prefastened absorbent article comprises;
    a) a pair of primary fasteners which are located on said opposed side edges in said back waist region and which overlap and releasably engage said front waist region of said absorbent article to provide said prefastened absorbent article;
    b) a belt located in said back waist region which is capable of being elongated and which provides a pretension on said back waist region when said primary fasteners are releasably engaged, said belt including opposed end portions, a latent segment and an elastic segment; and
    c) a pair of slots through which said opposed end portions of said belt slidably extend.

2. The absorbent article of claim 1 wherein said latent segment of said belt is a latent elastic material.

3. The absorbent article of claim 1 wherein said elastic segment is a neck bonded laminate material.

4. The absorbent article of claim 1 and further comprising at least one secondary fastener located on one of said end portions of said belt which is configured to releasably engage said front waist region to conform said waist regions to said wearer's body after said prefastened absorbent article is pulled on over a wearer's hips.

5. A package of prefastened disposable absorbent articles containing two or more absorbent articles according to claim 1.

6. The absorbent article of claim 1 wherein said latent segment is a latent, relatively inelastic material.

7. The absorbent article of claim 6 wherein said latent segment is a film material.

8. The absorbent article of claim 1 wherein said belt defines a first length when applied to said absorbent article and a second length which is less than said first length after said latent segment is activated to provide said pretension on said back waist region.

9. The absorbent article of claim 8 wherein said second length is less than about 90 percent of said first length.

10. The absorbent article of claim 8 wherein said belt is capable of being elongated to a third length which is greater than said first length.

11. The absorbent article of claim 10 wherein said third length is at least about 105 percent of said first length.

12. A prefastened disposable absorbent article which defines an absorbent, a front waist region, a back waist region, a crotch region which extends between and connects said waist regions and a pair of opposed side edges wherein said prefastened absorbent article comprises:
    a) a pair of primary fasteners which are located on said opposed side edges on said waist region and which are releasably engaged to said front waist region to provide said prefastened absorbent article;
    b) a belt located in said back waist region which defines opposed end portions, a latent segment and an elastic segment, said belt providing a pretension on said back waist region when said primary fasteners are releasably engaged and said belt being capable of elongation; and
    c) a pair of secondary fasteners which are located on said opposed end portions of said belt and which are configured to releasably engage said front waist region to conform said waist regions to a wearer's body after said prefastened absorbent article is pulled on over a wearer's hips.

13. The absorbent article of claim 12 wherein said latent segment of said belt is a latent elastic material.

14. The absorbent article of claim 12 wherein said elastic segment is a neck bonded laminate material.

15. The absorbent article of claim 12 wherein said belt includes two of said elastic segments wherein said latent segment is located between said two elastic segments and wherein said elastic segments include said opposed end portions to which said secondary fasteners are attached.

16. The absorbent article of claim 12 wherein said secondary fasteners and said opposed end portions of said belt are configured to extend over said primary fasteners to releasably engage said front waist region of said absorbent article to conform said waist regions to said wearer's body after said prefastened absorbent article is pulled on over a wearer's hips.

17. A package of prefastened disposable absorbent articles containing two or more absorbent articles according to claim 12.

18. The absorbent article of claim 12 wherein said latent segment is a latent, relatively inelastic material.

19. The absorbent article of claim 18 wherein said latent segment is a film material.

20. The absorbent article of claim 12 wherein said belt defines a first length when applied to said absorbent article and a second length which is less than said first length after said latent segment is activated to provide said pretension on said back waist region.

21. The absorbent article of claim 20 wherein said second length is less than about 90 percent of said first length.

22. The absorbent article of claim 20 wherein said belt is applied to said absorbent article in an untensioned, nonelongated state to define said first length.

23. The absorbent article of claim 20 wherein said belt is capable of being elongated to a third length which is greater than said first length.

24. The absorbent article of claim 23 wherein said third length is at least about 105 percent of said first length.

25. A prefastened disposable absorbent article which defines a front waist region, a back waist region, a crotch region which extends between and connects said waist regions and a pair of laterally opposed side edges, said absorbent article comprising:
   a) an outer cover;
   b) an absorbent chassis which is connected to said outer cover and which includes a bodyside liner and an absorbent core disposed between said outer cover and said bodyside liner;
   c) a pair of primary fasteners which are located on said laterally opposed side edges of said back waist region of said absorbent article and which are configured to releasably engage an outer surface of said absorbent article in said front waist region of said absorbent article;
   d) a belt which is located in said back waist region of said absorbent article and which defines a pair of opposed end portions, a pair of opposed elastic segments and a latent segment between said elastic segments; and
   e) a pair of secondary fasteners which are located on said opposed end portions of said belt and which are configured to releasably engage said outer surface of said front waist region to further conform said waist regions to a wearer's body after said prefastened absorbent article is pulled on over a wearer's hips.

26. The absorbent article of claim 25 wherein said latent segment of said belt is a latent elastic material.

27. The absorbent article of claim 25 wherein said elastic segments are a neck bonded laminate material.

28. The absorbent article of claim 25 wherein said secondary fasteners and said opposed end portions of said belt are configured to extend over said primary fasteners to releasably engage said front waist region of said absorbent article to conform said waist regions to said wearer's body after said prefastened absorbent article is pulled on over a wearer's hips.

29. A package of prefastened disposable absorbent articles containing two or more absorbent articles according to claim 25.

30. The absorbent article of claim 25 wherein said latent segment is a latent, relatively inelastic material.

31. The absorbent article of claim 30 wherein said latent segment is a film material.

32. The absorbent article of claim 25 wherein said belt defines a first length when applied to said absorbent article and a second length which is less than said first length after said latent segment is activated to provide a pretension on said back waist region.

33. The absorbent article of claim 32 wherein said belt is applied to said absorbent article in an untensioned, nonelongated state to define said first length.

34. The absorbent article of claim 25 wherein said absorbent article includes a carrier panel located on a bodyfacing side of said outer cover in said one back waist region, wherein said opposed elastic segments of said belt are attached to said carrier panel at spaced apart locations and a portion of said carrier panel extending between said elastic segments provides said latent segment of said belt.

35. The absorbent article of claim 34 wherein said carrier panel is a latent material.

36. The absorbent article of claim 34 wherein said carrier panel includes a latent material between two opposed nonlatent materials.

37. The absorbent article of claim 32 wherein said second length is less than about 90 percent of said first length.

38. The absorbent article of claim 37 wherein said belt is capable of being elongated to a third length which is greater than said first length.

39. The absorbent article of claim 38 wherein said third length is at least about 105 percent of said first length.

40. A prefastened disposable absorbent article which defines an absorbent, a front waist region, a back waist region, a crotch region which extends between and connects said waist regions and a pair of opposed side edges wherein said absorbent article comprises:
   a) a pair of primary fasteners which are located on said opposed side edges in said back waist region and which are releasably engaged to said front waist region of said disposable absorbent article thereby defining a waist perimeter dimension; and
   b) a waist size adjustment means located in said back waist region for providing an initial pretension on said waist regions of said absorbent article when said absorbent article is at said waist perimeter dimension and for reducing said waist perimeter dimension of said absorbent article without releasing said primary fasteners to conform said waist regions to a wearer's body after said prefastened absorbent article has been pulled on.

41. The absorbent article of claim 40 wherein said waist size adjustment means includes:
   a) a belt which is located in said back waist region wherein said belt defines opposed elastic segments and a latent segment located between said elastic segments; and
   b) a pair of secondary fasteners which are located on said opposed elastic segments of said belt and which are configured to releasably engage said front waist region to conform said waist regions to said wearer's body.

42. A prefastened disposable absorbent article which defines an absorbent, a front waist region, a back waist region, a crotch region which extends between and connects said waist regions and a pair of opposed side edges wherein said prefastened absorbent article comprises:
   a) a pair of primary fasteners which are located on said opposed side edges in said front waist region and which overlap and releasably engage said back waist region of said absorbent article to provide said prefastened absorbent article;
   b) a belt located in said front waist region which is capable of being elongated and which provides a pretension on said front waist region when said primary fasteners are releasably engaged, said belt including opposed end portions, a latent segment and an elastic segment; and
   c) a pair of slots through which said opposed end portions of said belt slidably extend.

43. A prefastened disposable absorbent article which defines an absorbent, a front waist region, a back waist region, a crotch region which extends between and connects said waist regions and a pair of opposed side edges wherein said prefastened absorbent article comprises:
   a) a pair of primary fasteners which are located on said opposed side edges on said front waist region and which are releasably engaged to said back waist region to provide said prefastened absorbent article;
   b) a belt located in said front waist region which defines opposed end portions, a latent segment and an elastic segment, said belt providing a pretension on said front waist region when said primary fasteners are releasably engaged and said belt being capable of elongation; and
   c) a pair of secondary fasteners which are located on said opposed end portions of said belt and which are configured to releasably engage said back waist region to conform said waist regions to a wearer's body after said prefastened absorbent article is pulled on over a wearer's hips.

* * * * *